US008313767B2

(12) United States Patent
Mizushima et al.

(10) Patent No.: US 8,313,767 B2
(45) Date of Patent: Nov. 20, 2012

(54) DRUG-CONTAINING SUSTAINED RELEASE MICROPARTICLE, PROCESS FOR PRODUCING THE SAME AND PREPARATION CONTAINING THE MICROPARTICLE

(75) Inventors: Yutaka Mizushima, Tokyo (JP); Yasuaki Ogawa, Kyoto (JP); Junzo Tanaka, Tsukuba (JP); Toshiyuki Ikoma, Tsukuba (JP)

(73) Assignee: Independent Administrative Institution, National Institute for Materials Science, Ibaraki (JP)

( * ) Notice: Subject to any disclaimer, the term of this patent is extended or adjusted under 35 U.S.C. 154(b) by 166 days.

(21) Appl. No.: 12/837,810

(22) Filed: Sep. 2, 2010

(65) Prior Publication Data
US 2010/0322902 A1    Dec. 23, 2010

Related U.S. Application Data

(63) Continuation of application No. 10/559,512, filed on Dec. 5, 2005, now abandoned.

(30) Foreign Application Priority Data

Jun. 18, 2003    (JP) .................................. 2003-173431

(51) Int. Cl.
| | | |
|---|---|---|
| A61K 9/22 | (2006.01) | |
| A61K 9/14 | (2006.01) | |
| A61K 33/30 | (2006.01) | |
| A61K 38/00 | (2006.01) | |
| A61K 31/70 | (2006.01) | |
| A61K 31/7088 | (2006.01) | |
| A61K 31/56 | (2006.01) | |
| A61K 31/315 | (2006.01) | |

(52) U.S. Cl. ......... 424/468; 424/489; 424/641; 514/1.1; 514/44 A; 514/169; 514/494

(58) Field of Classification Search .................. 424/468, 424/489, 641; 514/1.1, 44 A, 169, 494
See application file for complete search history.

(56) References Cited

U.S. PATENT DOCUMENTS

| 4,157,378 | A | 6/1979 | Tomlinson et al. |
|---|---|---|---|
| 7,378,394 | B2 | 5/2008 | Ogawa et al. |
| 2004/0180091 | A1 | 9/2004 | Lin |
| 2006/0093670 | A1 | 5/2006 | Mizushima et al. |

FOREIGN PATENT DOCUMENTS

| JP | 59101145 | 6/1984 |
|---|---|---|
| JP | 3218310 | 9/1991 |
| JP | 4327525 | 11/1992 |
| JP | 9165327 | 6/1997 |
| JP | 11286403 | 10/1999 |
| JP | 2000239104 | 9/2000 |
| JP | 2002020218 | 1/2002 |
| JP | 2002326960 | 11/2002 |
| JP | 2004075662 | 3/2004 |
| WO | 9809645 | 3/1998 |
| WO | 2004000270 | 12/2003 |

OTHER PUBLICATIONS

Online Merck Manual Home Health Edition article entitled, "Atherosclerosis" accessed on Apr. 17, 2002 at www.merckmanuals.com/home/print/heart_and_blood_vessel_disorders/atherosclerosis/atherosclerosis.html.*
Online Merck Manual Home Health Edition, "Hemophilia," www.merckmanuals.com/home/print/blood_disorders/bleeding_and_clotting_disorders/hemophilia.html accessed on Apr. 17, 2002.*
Online Merck Manual Home Health Edition, "Sepsis and Septic Shock," accessed on Apr. 17, 2012 at www.merckmanuals.com/home/infections/bacteremia_sepsis_and_septic_shock/sepsis_and_septic_shock.html#v784628.*
Johnson, "A Month-Long Effect From a Single Injection of Microencapsulated Human Growth Hormone," Nature Medicine, vol. 2, No. 7, Jul. 1996, pp. 795-799.
Ogawa et al., "A New Technique to Efficiently Entrap Leuprolide Acetate into Microcapsules of Polylactic Acid or Copoly(Lactic/Glycolic) Acid," Chemical Pharmaceutical Bulletin, vol. 36, No. 3, 1988, pp. 1095-1103.
Gautier et al., "In Vitro Influence of Apatite-granule-specific Area on Human Growth Hormone Loading and Release," Journal of Biomedical Materials Research, vol. 34, No. 2, 1997, pp. 165-170.
Guicheux et al., "Apatite as Carrier for Growth Hormone: In Vitro Characterization of Loading and Release," Journal of Biomedical Materials Research, vol. 34, No. 2, 1997, pp. 165-170.
Yamaguchi et al., "Ceramic Science Series 7 Bioceramics," Gihodo Shuppan Co., Ltd., 1984, pp. 7-9.

* cited by examiner

*Primary Examiner* — James H Alstrum Acevedo
(74) *Attorney, Agent, or Firm* — Price Heneveld LLP

(57) ABSTRACT

Sustained release microparticles suitable for various types of drugs, or drug-containing sustained release microparticles capable of sustained release of drugs over a period of three days or more and capable of inhibiting initial burst release; a process for producing the same; and preparations containing the microparticles are disclosed. The drug-containing sustained release microparticles comprise a drug other than human growth hormone and a porous apatite derivative, and optionally include a water-soluble bivalent metal compound. The drug-containing sustained release microparticles can be produced by dispersing under agitation microparticles of a porous apatite derivative in an aqueous solution containing a drug so that the aqueous solution infiltrates into the porous apatite derivative; optionally adding an aqueous solution containing a water-soluble bivalent metal compound that may infiltrate into the porous apatite derivative; further adding additives such as a stabilizer to the mixture; and effecting lyophilization or vacuum drying.

11 Claims, 1 Drawing Sheet

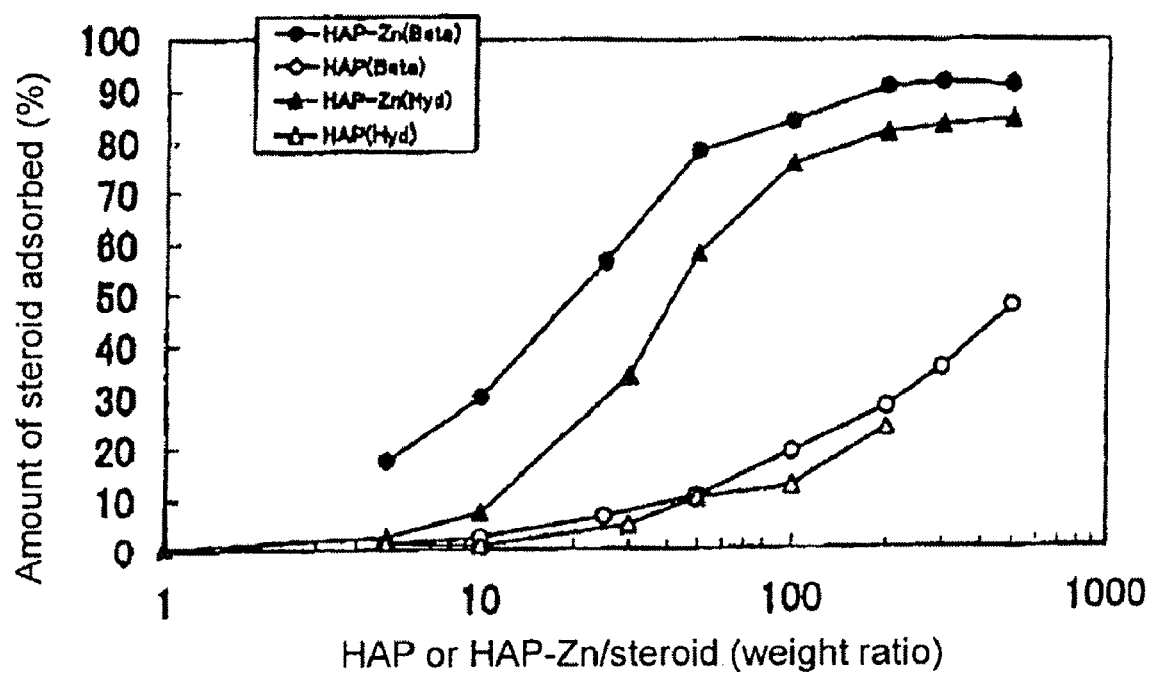

DRUG-CONTAINING SUSTAINED RELEASE MICROPARTICLE, PROCESS FOR PRODUCING THE SAME AND PREPARATION CONTAINING THE MICROPARTICLE

CROSS REFERENCE TO RELATED APPLICATION

This application is a continuation of U.S. patent application Ser. No. 10/559,512 entitled "Drug-Containing Sustained Release Microparticle, Process for Producing the Same and Preparation Containing the Microparticle" which was filed on Dec. 5, 2005, now abandoned.

TECHNICAL FIELD

The present invention relates to drug-containing sustained release microparticles comprising, as a base, microparticles of a porous apatite derivative that disappears in a living body; a process for producing the same; and a preparation containing the microparticles.

BACKGROUND ART

Investigation has heretofore been made on particulate injections that provide the sustained release of drugs for a long period, most of which comprise poly-lactic-co-glycolic acid (PLGA) as a base (see Japanese Patent Laid-Open Nos. 11-286403, 2000-239104 and 2002-326960). Alternatively, sustained release microcapsules that contain human growth hormone (hGH) and comprise PLGA as a base have been reported (Nature Medicine, 2: 795-799, 1996). Sustained release microcapsules that contain leuprorelin, a LHRH agonist, and comprise PLGA as a base have also been reported (Chemical Pharmaceutical Bulletin, 36: 1095-1103, 1988). PLGA is a biodegradable base that hydrolyzes and disappears in a living body, and this property is preferable for a base of an injection. However, if drugs encapsulated in typical sustained release particulate preparations that use PLGA are highly soluble in water, there is an inevitable problem with excessive release in the early stage of administration (initial burst). In addition, organic solvents must be used for its production. In this case, inactivation becomes a problem for protein drugs. Furthermore, if a solvent evaporation method typically used as a production process is adopted, the amount of drugs encapsulated, in the case of water-soluble drugs, is 10% or less by weight, and the amount of the whole preparation administered, in the case of drugs with low activity, is increased. Such a preparation is difficult to administer. Because the preparation has a relatively large average particle size of 20 µm or more, an injection needle as thick as 21 to 23 G is required. Some sustained release particles of drugs that use hydroxyapatite have already been reported (H. Gautier et al., Journal of Biomedical Material Research, 40, 606-613, 1998; and J. Guicheux et al., Journal of Biomedical Material Research, 34, 165-170, 1997). However, all of the sustained release particles are two-component systems having the drug and hydroxyapatite, in which hydroxyapatite has a large particle size of 40 to 80 µm or 200 µm and their in-vivo sustained release effect is unknown. Besides, the amount of the drug adsorbed into the apatite particle (the amount of the drug encapsulated) was as low as 1% or less.

BRIEF DESCRIPTION OF THE DRAWING

FIG. 1 is a graph showing the amount of steroid absorbed in a porous hydroxyapatite (HAP) and a porous hydroxyapatite (HAP-Zn) with substitution of zinc as a function of the weight ratio of HAP or HAP-Zn to steroid.

DISCLOSURE OF THE INVENTION

A material having so-called biodegradability or a property of disappearing in a living body, which disappears from a living body within a period of time near the end of the release of drugs after administration, must be selected as a sustained release base. Initial burst release (the excessive release of drugs in the early stage of administration), with respect to highly water-soluble drugs as well, must be small. Taking protein drugs into consideration, a sustained release base and a process for producing drug-containing sustained release microparticles, which allow production with the minimal use of organic solvents, must be found. Particulate preparations capable of easily passing through a thin injection needle of 23 G or less and capable of sustained release of drugs over a period of three days must be prepared, wherein the amount of drugs encapsulated in the drug-containing microparticle is brought to 10% or more by weight.

In order to solve these problems, the present inventors have found that sustained release microparticles suitable for various types of drugs can be obtained by use of microparticles of a porous apatite derivative. The present inventors have further found that the use of a water-soluble bivalent metal compound in combination with a drug other than human growth hormone achieves the sustained release of the drug over a period of three days or more and inhibits, with respect to highly water-soluble drugs as well, initial burst release. In addition, the present inventors have found that when the water-soluble bivalent metal compound is not used, the same effect can be obtained.

Thus, an object of the present invention is to provide sustained release microparticles suitable for various types of drugs, or drug-containing sustained release microparticles capable of sustained release of drugs over a period of three days or more and capable of preventing, with respect to highly water-soluble drugs as well, initial burst release; a process for producing the same; and preparations containing the microparticles.

The drug-containing sustained release microparticles of the present invention comprise a drug other than human growth hormone and a porous apatite derivative, or comprise a drug other than human growth hormone, a porous apatite derivative and a water-soluble polyvalent metal compound. The water-soluble polyvalent metal compound includes zinc chloride, calcium chloride, calcium hydroxide, iron chloride, iron hydroxide, cobalt chloride, aluminum chloride and zinc acetate. Among others, a water-soluble bivalent compound is most preferred. The preferred water-soluble bivalent compound includes a zinc compound and a calcium compound, with zinc chloride most preferred. In addition, zinc acetate, calcium chloride, and the like are also preferred.

The preparation for parenteral administration of the present invention comprises the drug-containing sustained release microparticles.

It is preferred that the preparation for parenteral administration should be a subcutaneous injection or an intramuscular injection.

It is also preferred that the porous apatite derivative should be a porous apatite derivative in which a portion of calcium as a constituent in the composition of hydroxyapatite is substituted with zinc during production.

Moreover, it is preferred that the zinc substitution rate or zinc content rate in the porous apatite derivative should be 0.1 to 2.0.

The process for producing the drug-containing sustained release microparticles of the present invention comprises: dispersing under agitation microparticles of a porous apatite derivative in an aqueous solution containing a drug so that the aqueous solution infiltrates into the porous apatite derivative; adding thereto an aqueous solution containing a water-soluble bivalent metal compound so that the water-soluble bivalent metal compound infiltrates into the porous apatite derivative; further adding an additive such as a stabilizer to the mixture; and effecting lyophilization or vacuum drying.

In some cases, the process for producing drug-containing sustained release microparticles does not involve the addition of the aqueous solution containing the water-soluble bivalent metal compound. Therefore, the water-soluble bivalent metal compound does not infiltrate in the porous apatite derivative.

Likewise, it is preferred for the process for producing drug-containing sustained release microparticles that: the porous apatite derivative should be a porous apatite derivative in which a portion of calcium as a constituent of hydroxyapatite is substituted with zinc during production; the zinc substitution rate or zinc content rate in the porous apatite derivative should be 0.1 to 2.0; and the water-soluble bivalent metal compound should be zinc chloride or zinc acetate.

The drug other than human growth hormone used herein is not particularly limited and is preferably a water-soluble drug. For example, a protein drug includes interferons, interleukins, G-CSF, BDNF, FGF, EGF and a variety of antibodies. A peptide drug includes GnRH and its derivatives, TRH, enkephalins, PTH and calcitonin. A DNA-associated substance includes antisense and ribozyme. In addition, anti-inflammatory drugs, steroids, anti-dementia drugs and drugs for circulatory diseases are encompassed.

In the basic process for producing drug-containing sustained release microparticles, microparticles of a porous apatite derivative is dispersed under agitation in an aqueous solution containing a drug so that the aqueous solution sufficiently infiltrates into the porous apatite derivative. An aqueous solution containing a water-soluble bivalent metal compound is further added thereto so that the water-soluble bivalent metal compound sufficiently infiltrates into the porous apatite derivative. Then, appropriate additives such as a stabilizer are added to the mixture. Lyophilization or vacuum drying is effected, thereby obtaining a powder of drug-containing sustained release microparticles comprising the drug and the microparticles of the porous apatite derivative as a base. When actually administered, this obtained powder is dispersed in an appropriate dispersion medium and injected, for example, subcutaneously or intramuscularly. When the desorption of the encapsulated drug is measured by dispersing the microparticles thus obtained in a large amount of purified water at room temperature, the drug up to a certain amount relative to porous apatite derivatives was not desorbed, though depending on the type of the drug. That is, the drug probably infiltrates and is adsorbed in the fine pores of the porous apatite derivatives.

The microparticles of the porous apatite derivative used herein can be obtained by a known method including a method described in, for example, T. Yamaguchi, H. Yanagida, A. Makishima, H. Aoki, Ceramic Science Series 7 Bioceramics, GIHODO SHUPPAN Co., Ltd., pp. 7-9, 1984. The most preferable porous apatite derivative is any of those in which a portion of Ca in the composition of hydroxyapatite is substituted with zinc (Zn). The rate of substitution (the number of a Zn atom relative to 10 Ca atoms) is preferably 0.1 to 5.0, more preferably 0.1 to 2.0. In this case, the disappearing velocity of the porous apatite derivative in a living body differs depending on the ratio of $(Ca+Zn)/P$. If the ratio is smaller than 1.67, the porous apatite derivative is more likely to be soluble in water, that is, the disappearing velocity of the porous apatite derivative in a living body is accelerated. It is preferred that the ratio of $(Ca+Zn)/P$ should fall within the range of 1.67 to 1.51. When the porous apatite derivative is used within this range, the porous apatite derivative disappears in a living body within a few weeks to a few months. The substitution rate or content rate (the number of a Zn atom relative to 10 Ca atoms) is preferably 0.1 to 5.0, more preferably 0.1 to 2.0. A lower treating temperature at which the porous apatite derivative is produced renders the porous apatite derivative more soluble in water and therefore accelerates the disappearing velocity of the porous apatite derivative in a living body. The treating temperature used is room temperature to 800° C., preferably 150° C. to 600° C. More preferable is a treating temperature of 150° C. to 400° C. If the porous apatite derivative is treated at 800° C. or higher, the resulting porous apatite derivative does not disappear in a living body. The particle size of the microparticle can be controlled by a treating temperature and can be used in the range of 0.1 µm to 100 µm. Of these sizes, preferred is 0.1 µm to 20 µm. The microparticle having a particle size of 0.2 µm to 10 µm can be utilized more preferably.

The rate of the drug adsorbed into the porous apatite derivative is much larger than the rate of the drug adsorbed into hydroxyapatite without Zn substitution. This is attributed to the specific surface and porosity of the porous apatite derivative that are significantly increased by allowing the porous apatite derivative to undergo zinc substitution or to contain zinc. The larger rate of the drug adsorbed is preferred because the gross amount of the drug-containing sustained release microparticles administered is rendered smaller. The preferred rate of the drug adsorbed differs depending on the optimal amount of the drug administered and however, is generally 2 to 30% by weight relative to porous apatite derivatives. Of these rates, 5 to 25% by weight is preferably used. More preferred is any of those adsorbing 10% or more by weight of the drug therein.

The water-soluble bivalent metal compound that is added after drugs are adsorbed into porous apatite derivatives is preferably a Zn or Ca compound. Of them, the Zn compound is most preferable. The amount of its usage, which varies depending on the physicochemical property of the drug, is generally in the range of 1 to 70% by weight relative to the porous apatite derivative and is preferably in the range of 5 to 70% by weight for sufficiently maintaining the sustained release of drugs. A chloride or a salt of an organic acid is preferably selected as the water-soluble bivalent metal compound used. Examples thereof include zinc chloride, zinc acetate and calcium chloride.

The duration of sustained release of drugs from the drug-containing sustained release microparticles thus obtained, can be controlled by the treating temperature of a hydroxyapatite derivative and the amount of the bivalent metal compound used, and may extend a period of three days or more. The sustained release of drugs over a period of one week or more is also made possible and is preferable in practice.

The drug-containing sustained release microparticle finally obtained may have a size that allows the microparticle to pass through an injection needle used in typical administration. In reality, the smaller size an injection needle has, the less a patient is scared. It is preferred that the drug-containing sustained release microparticle should pass through an injection needle with a thickness of 25 G or smaller (the larger the number is, the thinner an injection needle gets) defined by the international standard that specifies the thickness of an injection needle. For this reason, a drug-containing sustained release microparticle having a smaller particle size is more preferable. However, a drug-containing sustained release microparticle having a particle size rendered small to the extreme reduces the amount of drugs retained therein and increases initial burst release. Actually, the particle size is preferably 0.5 μm to 20 μm, more preferably 0.5 μm to 10 μm. A microparticle having a particle size of 10 μm or less easily passes through a 27-G injection needle. The drug used herein is not particularly limited as long as the drug is water-soluble and may be adsorbed into porous apatite derivatives. A water solubility index can be evaluated by solubility in water. As long as the solubility is 100 μg/mL or more, the drug-containing sustained release microparticle can be prepared in general. The solubility is more preferably 500 μg/mL or more, even more preferably 1 mg/mL.

EXAMPLES

Hereinafter, the present invention will be described in detail with reference to Examples. However, the present invention is not intended to be limited to these Examples.

Example 1

A betamethasone phosphate or hydrocortisone phosphate aqueous solution (100 μL, 100 μg/mL) was mixed with a water suspension (100 μL) of a given amount of porous hydroxyapatite (HAP) or porous apatite derivative with substitution by 0.5 mol of zinc (HAP-Zn-0.5) and left at room temperature for 10 minutes, followed by centrifugation at 2500 G to determine betamethasone phosphate or hydrocortisone phosphate liberated in the resulting supernatant from the absorbance of the supernatant at 230 nm. The amount of the drug remaining after the given amount of the drug initially applied washed away in the supernatant was used as the amount of the drug adsorbed. The result is shown in FIG. 1. As can be seen from FIG. 1, a larger amount of the HAP or the porous apatite derivative relative to the drug allowed the adsorption of the drug into the HAP or the porous apatite derivative at a higher ratio. The porous apatite derivative had an adsorption ratio significantly higher than that of the HAP.

In FIG. 1, Beta represents betamethasone phosphate, and Hyd represents hydrocortisone phosphate. Steroid refers to betamethasone phosphate or hydrocortisone phosphate.

Example 2

After 45 mg of porous hydroxyapatite (HAP) or porous apatite derivative (derivative with substitution by or content of 0.5 mol of zinc (HAP-Zn-0.5)) was accurately weighed and supplemented with 2.4 mg/mL interferon α (IFN) solution (30 μg in terms of the amount of IFN), the resulting mixture was left for 10 minutes. This mixture was then supplemented with 1 mL of 20 mM zinc acetate solution and shaken for 30 minutes. This dispersion was supplemented with 1.5 mL of water and washed to quantify IFN in the washed solution. As a result, IFN was not detected in both of the HAP and the HAP-Zn-0.5. Namely, it was confirmed that the whole amount of IFN was adsorbed into the HAP or the HAP-Zn-0.5. As described above, the drug-containing microparticle in which IFN, a protein, was adsorbed could be obtained without the use of organic solvents. After washing, 20 mL of a PBS solution containing 20% FCS was added to the obtained powder and shaken at 37° C. for 16 hours. IFN eluted into the resulting supernatant was determined to calculate the rate of elution. The result is shown in Table 2.

TABLE 1

Rate of elution of IFN adsorbed into HAP and HAP-Zn-0.5

|  |  |  | Rate of IFN eluted (%) |
|---|---|---|---|
| HAP | Zinc acetate | 0 mM | 92 |
|  | Zinc acetate | 20 mM | 87 |
| HAP-Zn-0.5 | Zinc acetate | 0 mM | 89 |
|  | Zinc acetate | 20 mM | 78 |

In all of the systems, the addition of zinc acetate allowed the inhibition of the elution of IFN and the sustained release of IFN for a longer period as compared with no addition of zinc acetate. When the HAP and the HAP-Zn-0.5 were compared, it was apparent that the HAP-Zn-0.5 more delayed elution and exhibited the sustained release of IFN for a longer time.

The invention claimed is:

1. Drug-containing sustained release microparticle preparation of a drug other than human growth hormone characterized in that a drug other than human growth hormone and a water-soluble bivalent metal compound are absorbed to a zinc-containing porous hydroxyapatite which is formed by partially substituting calcium atoms of porous hydroxyapatite with zinc atoms.

2. The drug-containing sustained release microparticle preparation of a drug other than a human growth hormone accordingly to claim 1, characterized in that a number of atoms of zinc contained in the zinc-containing porous hydroxyapatite is 0.1 to 2.0 relative to 10 atoms of calcium of the porous hydroxyapatite.

3. The drug-containing sustained release microparticle preparation of a drug other than a human growth hormone according to claim 1, characterized in that the water-soluble bivalent metal compound is zinc chloride.

4. The drug-containing sustained release microparticle preparation of a drug other than a human growth hormone according to claim 1, characterized in that the content of the drug other than human growth hormone in the zinc-containing porous hydroxyapatite is from 2% to 30% by weight.

5. A drug-containing sustained release microparticle preparation comprising:

a drug selected from the group consisting of: protein drugs, peptide drugs, antisense drugs, ribozyme drugs, steroids, and anti-dementia drugs;

a porous hydroxyapatite derivative in which a portion of the calcium atoms in the composition of hydroxyapatite is substituted with zinc atoms such that the number of zinc atoms relative to ten calcium atoms is from 0.1 to 5.0; and a water-soluble bivalent metal compound, wherein the drug and the water-soluble bivalent metal compound are adsorbed into the pores of the hydroxyapatite derivative.

6. The drug-containing sustained release microparticle preparation of claim 5, wherein the water-soluble bivalent metal compound is zinc chloride.

7. The drug-containing sustained release microparticle preparation of claim 5, wherein the content of the drug in the zinc-containing porous hydroxyapatite is from 2% to 30% by weight.

8. A sustained release preparation of a drug, comprising:

a zinc-containing porous hydroxyapatite derivative in which a portion of calcium as a constituent in the composition of hydroxyapatite is substituted with zinc;

a water-soluble drug other than human growth hormone adsorbed in the zinc-containing porous hydroxyapatite derivative; and a water-soluble bivalent metal compound disposed in the zinc-containing porous hydroxyapatite derivative.

9. A preparation according to claim 8, in which the number of atoms of zinc contained in the zinc-containing porous hydroxyapatite is 0.1 to 2.0 relative to 10 atoms of calcium of the porous hydroxyapatite.

10. A preparation according to claim 8, in which the water-soluble bivalent metal compound is zinc chloride.

11. A preparation according to claim 8, in which the content of the drug other than human growth hormone in the zinc-containing porous hydroxyapatite is from 2% to 30% by weight.

* * * * *